US009833026B2

(12) United States Patent
Eppler, Jr. et al.

(10) Patent No.: US 9,833,026 B2
(45) Date of Patent: *Dec. 5, 2017

(54) SENSOR MODULE FOR SENSING FORCES TO THE HEAD OF AN INDIVIDUAL AND WIRELESSLY TRANSMITTING SIGNALS CORRESPONDING THERETO FOR ANALYSIS, TRACKING AND/OR REPORTING THE SENSED FORCES

(71) Applicant: Triax Technologies, Inc., Norwalk, CT (US)

(72) Inventors: William G. Eppler, Jr., Norwalk, CT (US); William D. Hollingsworth, Wilton, CT (US); John R. Pavlick, Jr., New Milford, CT (US)

(73) Assignee: Triax Technologies, Inc., Norwalk, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/285,251

(22) Filed: Oct. 4, 2016

(65) Prior Publication Data

US 2017/0020205 A1 Jan. 26, 2017

Related U.S. Application Data

(63) Continuation of application No. 14/464,074, filed on Aug. 20, 2014, now Pat. No. 9,462,839.

(Continued)

(51) Int. Cl.
| | | |
|---|---|---|
| *G08B 23/00* | (2006.01) | |
| *A41D 1/00* | (2006.01) | |
| *A42B 3/04* | (2006.01) | |
| *G08B 21/18* | (2006.01) | |
| *G01L 5/00* | (2006.01) | |
| *A41D 20/00* | (2006.01) | |
| *A42B 1/04* | (2006.01) | |
| *A42B 1/24* | (2006.01) | |

(Continued)

(52) U.S. Cl.
CPC ............. *A41D 1/002* (2013.01); *A41D 20/00* (2013.01); *A42B 1/041* (2013.01); *A42B 1/242* (2013.01); *A42B 3/046* (2013.01); *A61B 5/4088* (2013.01); *G01L 5/0052* (2013.01); *G08B 21/182* (2013.01); *G06F 19/3418* (2013.01)

(58) Field of Classification Search
CPC ................................ G08B 21/182; A42B 3/00
USPC ........... 340/539.12, 573.1, 665, 506; 702/42, 702/141; 600/587
See application file for complete search history.

(56) References Cited

U.S. PATENT DOCUMENTS 4,064,565 A 12/1977 Griffiths
5,978,972 A * 11/1999 Stewart .................. A42B 3/046
2/422

(Continued)

OTHER PUBLICATIONS

International Search Report and Written Opinion dated Nov. 24, 2014 in connection with International Application No. PCT/US2014/051919.

(Continued)

*Primary Examiner* — Phung Nguyen
(74) *Attorney, Agent, or Firm* — Wolf, Greenfield & Sacks, P.C.

(57) ABSTRACT

Sensor module for sensing forces to the head of an individual and wirelessly transmitting signals corresponding thereto for analysis, tracking and/or reporting the sensed forces.

21 Claims, 8 Drawing Sheets

Related U.S. Application Data

(60) Provisional application No. 61/881,275, filed on Sep. 23, 2013, provisional application No. 61/868,004, filed on Aug. 20, 2013.

(51) Int. Cl.
*A61B 5/00* (2006.01)
*G06F 19/00* (2011.01)

(56) References Cited

U.S. PATENT DOCUMENTS

| | | | | |
|---|---|---|---|---|
| 8,556,831 | B1* | 10/2013 | Faber | A42B 3/046 340/500 |
| 9,462,839 | B2 | 10/2016 | Eppler et al. | |
| 2005/0177335 | A1 | 8/2005 | Crisco et al. | |
| 2011/0181419 | A1 | 7/2011 | Mack et al. | |
| 2011/0219852 | A1 | 9/2011 | Kasten | |
| 2012/0143526 | A1* | 6/2012 | Benzel | A42B 3/046 702/42 |
| 2012/0155039 | A1 | 6/2012 | Jeftic-Stojanovski et al. | |
| 2012/0188083 | A1 | 7/2012 | Miller | |
| 2013/0013243 | A1 | 1/2013 | Levine et al. | |
| 2013/0053652 | A1 | 2/2013 | Cooner | |
| 2013/0060168 | A1 | 3/2013 | Chu et al. | |
| 2013/0110415 | A1 | 5/2013 | Davis et al. | |
| 2014/0247129 | A1* | 9/2014 | de la Fuente | A42B 3/046 340/573.1 |
| 2015/0077246 | A1 | 3/2015 | Eppler et al. | |
| 2015/0226621 | A1* | 8/2015 | Zhu | G01L 5/0052 702/41 |

OTHER PUBLICATIONS

International Preliminary Report on Patentability dated Mar. 3, 2016 in connection with International Application No. PCT/US2014/051919.

Extended European Search Report dated Mar. 23, 2017 in connection with European Application No. 14838682.4.

* cited by examiner

Sensor and data-collection overview:

SENSOR MODULE FOR SENSING FORCES TO THE HEAD OF AN INDIVIDUAL AND WIRELESSLY TRANSMITTING SIGNALS CORRESPONDING THERETO FOR ANALYSIS, TRACKING AND/OR REPORTING THE SENSED FORCES

CROSS-REFERENCE TO RELATED PATENT APPLICATIONS

This application is a continuation of and claims priority under §120 to U.S. patent application Ser. No. 14/464,074, entitled "SENSOR MODULE FOR SENSING FORCES TO THE HEAD OF AN INDIVIDUAL AND WIRELESSLY TRANSMITTING SIGNALS CORRESPONDING THERETO FOR ANALYSIS, TRACKING AND/OR REPORTING THE SENSED FORCES," filed Aug. 20, 2014, now U.S. Pat. No. 9,462,839. This application is a non-provisional of and claims priority under 35 U.S.C. §119(e) to U.S. Provisional Patent Application Ser. No. 61/881,275, entitled "SENSOR MODULE FOR SENSING FORCES TO THE HEAD OF AN INDIVIDUAL AND WIRELESSLY TRANSMITTING SIGNALS CORRESPONDING THERETO FOR ANALYSIS, TRACKING AND/OR REPORTING THE SENSED FORCES," filed Sep. 23, 2013; and U.S. Provisional Patent Application Ser. No. 61/868,004, entitled "SENSOR MODULE FOR SENSING FORCES TO THE HEAD OF AN INDIVIDUAL AND WIRELESSLY TRANSMITTING SIGNALS CORRESPONDING THERETO FOR ANALYSIS, TRACKING AND/OR REPORTING THE SENSED FORCES," filed Aug. 20, 2013, all of which applications are herein incorporated by reference in their entirety.

BACKGROUND OF THE INVENTION

Field of the Invention

The present invention relates to the sensing of forces to the head of an individual and, more particularly, to the use of a high-quality, mobile physiometric sensor module with a multi-layer distributed data storage, analysis and presentation structure.

Brief Discussion of the Related Art

Individuals engaged in a wide variety of physically demanding sports and activities risk brain or other serious injuries resulting from impact, hyper-extension and other extreme movements or events. Some examples of risk-laden sports include, among many others, football, soccer, baseball, basketball and rugby.

Most attempts to reduce the effects of impacts have included sensors mounted in helmets, in the mouth, or along the side of the head. They do not provide real-time information relating to occurrence of impact events to permit an individual being monitored to be removed from active play for the individual's safety.

SUMMARY OF THE INVENTION

The present invention senses forces applied to the head of an individual where indications of the sensed forces can be transmitted to one or more remote locations permitting visualizations of the force events to which an individual is exposed.

The present invention provides accurate sensing of force events and allows data analysis to be performed in real-time and, through more extensive postprocessing, to permit the warning of players, coaches, parents and others of events which are potentially harmful and could require medical attention. The present invention serves to protect all involved in sporting events or other activities, including players, coaches, managers and parents, for example, by informing them in real-time of impacts to an individual, assisting them in determining if or when the individual should be removed from the activity for the individual's safety.

Some of the advantages of the present invention include increasing athletic performance while decreasing risk, isolating players who have taken severe or repeated impacts to the head, reinforcement of proper techniques, providing coaches, trainers and parents confidence that they are making a game or activity safer. The sensing device or module, sometimes referred to as a SIM sensor, is carried on or in a support having a shape to surround the head, such as a headband or skull cap, not requiring a helmet or other special equipment, to transmit impacts to the head in real-time. The application of the present invention displays data in real-time for athletes on a team as well as for individual use, and stores data historically for each individual being monitored such that the data can be accessed for any time before or after an event for analysis by coaches, trainers, doctors, athletic directors and parents or the like. A software application that can be part of the present invention allows the present invention to be activated for the duration of a contact drill in practice such that any subsequent impact that occurs while the system is activated can be saved for later analysis relating to specific drills. Once a particular drill has been completed, head impacts that occurred during the drills can be isolated such that athletes recording the highest G-force impacts can be determined allowing a coach or others involved in the drill to apply special coaching to decrease the amount of impact to a particular athlete's head.

One aspect of the present invention is the positioning of the impact sensor module in alignment with the median nuchal line of the occipital bone of the skull thereby providing extremely accurate data. Positioning of the sensor can be accomplished by placing the sensor module in a pocket formed in a support having a shape to surround the head, such that the sensor module can be comfortably worn during activities at a position to record all impacts and accelerations greater than a preprogrammed set-point. The support can be formed of a headband, a skull cap, or fabric tied around the head like a bandana, and the pocket can be open to facilitate insertion of a sensor module or closed to form the sensor module integrally with the support.

In another aspect, the present invention allows the performance of cognitive and balance evaluation tests to gauge an individual's performance immediately after a possible concussive event in real-time. Balance evaluation tests can be accomplished with the sensor module in place by proper programming of the sensor module or by other equipment coordinating with the sensor module.

Another aspect of the present invention is a method for monitoring impact forces to the head utilizing a sensor module at the back of the head in alignment with the median nuchal line of the occipital bone utilizing local data service infrastructure and/or global data surface infrastructure.

In a further aspect, the present invention permits monitoring of impact forces to the head of individuals participating in a team activity where a sensor module is worn by each of the participants and a data collection wireless access point receives signals from the sensor modules.

Other aspects and advantages of the present invention will be appreciated from the following description of the invention taken in conjunction with the drawings. The drawings and the following description are meant to be exemplary only of an embodiment of the present invention.

DESCRIPTION OF THE INVENTION

Figure 1:
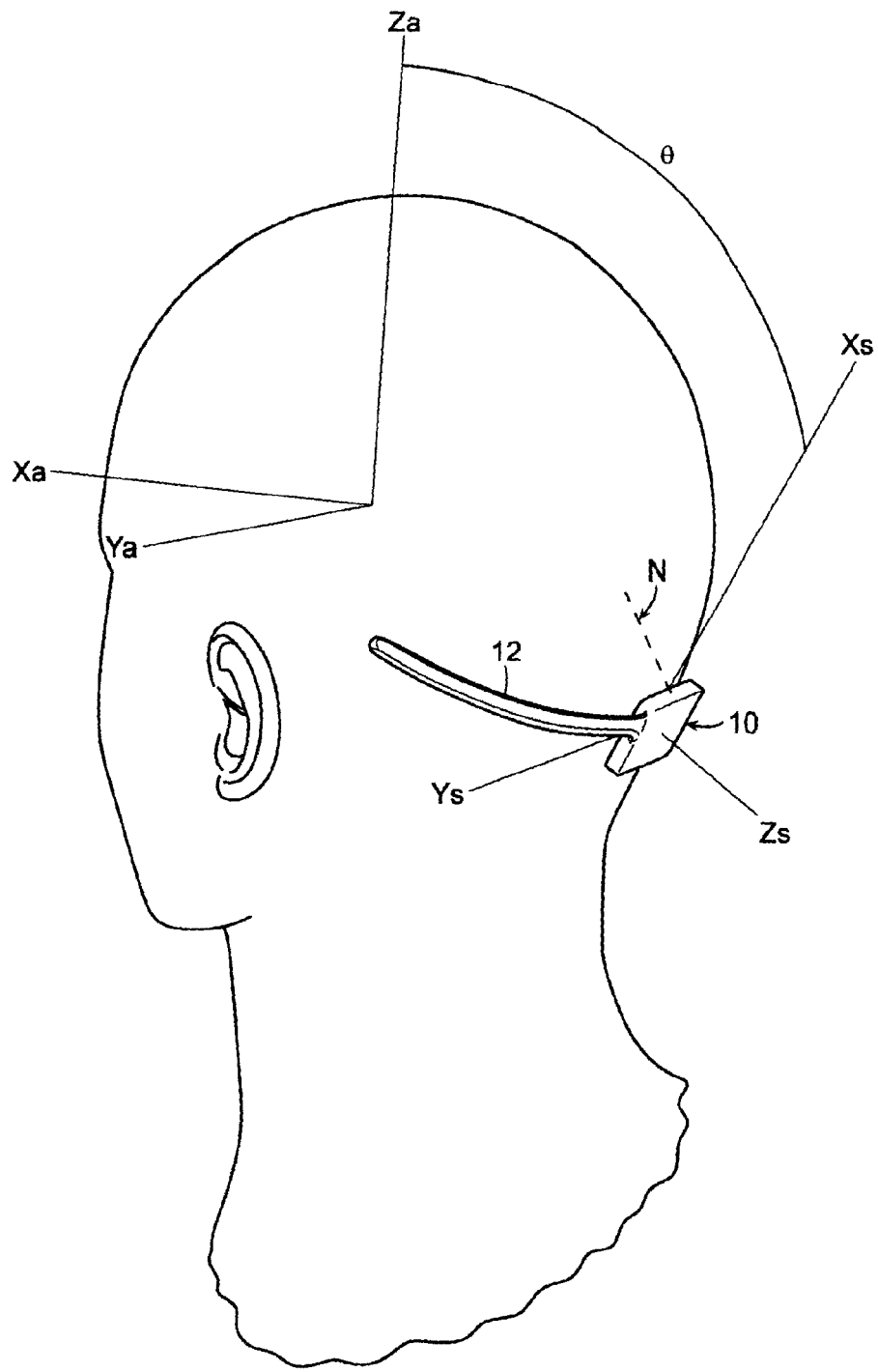
FIG. 1 is a perspective showing of a skull relative to a sensor module according to the present invention showing the positioning of the sensor module in substantial alignment with the median nuchal line of the occipital bone of the skull.

As shown in FIG. 1, a sensor module 10 in accordance with the present invention is typically a small, environmentally sealed device incorporating a sub GHz transceiver, a low power microprocessor, a 3-axis high g accelerometer, a 3-axis low g accelerometer, a 3-axis gyroscope, a non-volatile memory, a battery, a battery charger and other support circuitry. The sensor module 10 is sometimes referred to herein as a mobile sensor or a SIM or an impact monitor. The sensor module 10 is in substantial alignment with the median nuchal line of the occipital bone of the skull shown in dashed lines at N and, normally, between the inferior and superior nuchal lines. One embodiment utilizes a curved elongate antenna 12 extending from the sensor module housing toward the left side of the head. The anatomical axes denoted as $X_a$, $Y_a$ and $Z_a$, the sensor axes denoted as $X_s$, $Y_s$ and $Z_s$ and the subtended angle θ are illustrated in FIG. 1. The anatomical axes allow correlation with the axes in the sensor module.

Figure 2:
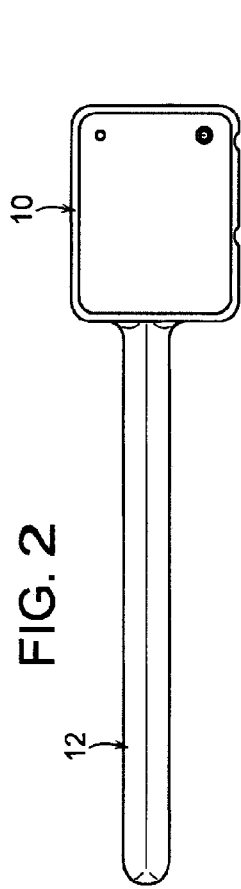
FIG. 2 is a plan view of a sensor module according to the present invention with an extended antenna.
Figure 3:
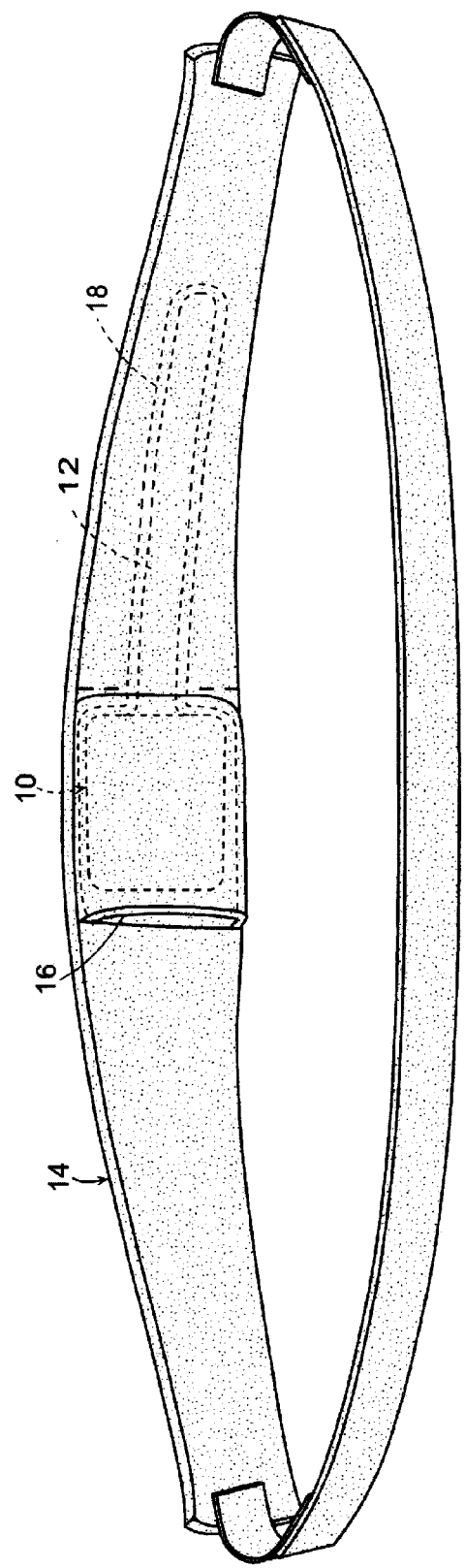
FIG. 3 is a perspective view of a headband with the sensor module of FIG. 2 held in a pocket therein.

A headband 14 is shown in FIG. 3 and has a pocket 16 arranged along an inner surface or lining and cooperating with an elongated arcuate pocket 18 such that the sensor module 10 and antenna 12 shown in FIGS. 1 and 2 can be inserted within the pocket 16 and arcuate space 18 such that the sensor module is positioned adjacent the skull. The headband is preferably made of a non-stretchable material having only a small section thereof made of elastic to allow for form fitting. The headband thus stabilizes the sensor module and prevents "double hit" sensing by keeping the sensor module firmly in place against the skull. The outer surface of the headband adjacent the pocket 16 can carry indicia I to facilitate accurate location of the sensor module on the head. The indicia can also include an arrow to make certain that the headband is properly oriented.

Figure 4:
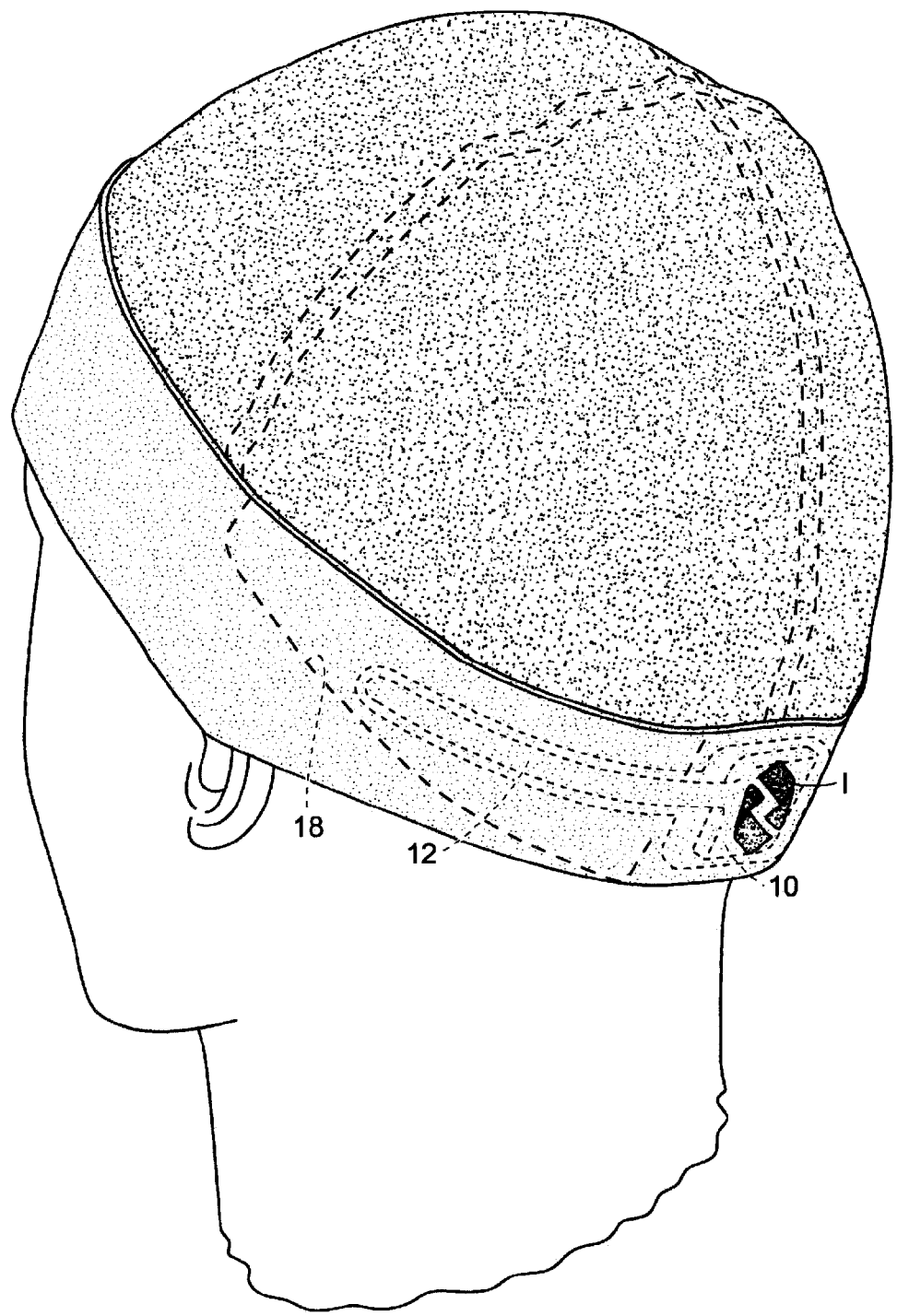
FIG. 4 is a perspective view of a skull cap on a head and holding the sensor module shown in FIG. 2.

A skull cap having a structure around the periphery including the pocket structure described above is shown in FIG. 4.

The sensor module communicates with an access point in a wireless fashion such as over the 915 MHz ISM band in the U.S. Other bands are possible through minor firmware and hardware changes over the frequency range of 300 MHz-348 MHz, 389 MHz-464 MHz and 779 MHz-928 MHz. The sensor module 10 is capable of measuring linear acceleration events up to +/−400 G and rotational velocities up to +/−2000°/sec at a 1 KHz sample rate. An "event" is defined as a 3-axis G recording of 10 ms before and 52 ms after a threshold is exceeded. The threshold is calculated as $(xg^2 + y_g^2 + zg^2)$ and is adjustable. When an event is detected, the event is transmitted wirelessly in real-time (within a few tenths of a second) to the access point. If wireless communication with the access point is interrupted, the event is stored in internal non-volatile memory. When wireless communication is restored, any saved events are transmitted.

Figure 5:
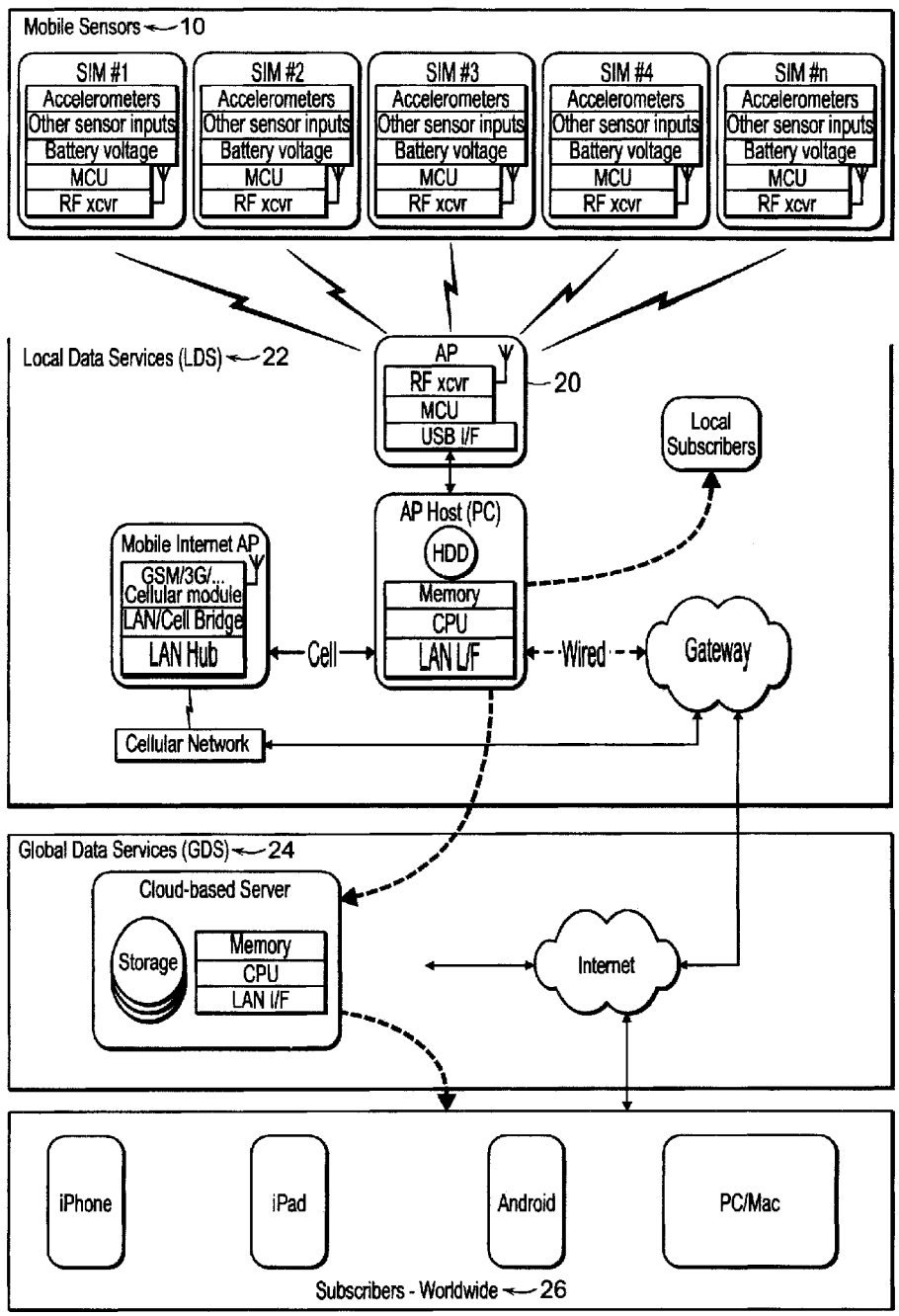
FIG. 5 is a block diagram of a system according to the present invention utilizing a plurality of sensor modules.

As shown in FIG. 5, the system of the present invention includes, in an exemplary embodiment, a plurality of sensor modules each in communication with an appropriate access point 20. Multiple impact monitors 10 can be used concurrently with a single access point 20. The access point and its associated impact monitors are assigned primary and secondary communication channels (from a set of over 30 for the 915 MHz band). If communication is not established on the primary channel within a few seconds, the impact monitors try on the secondary channel. This procedure is repeated until communication is established. The communication protocol is packet based with robust error checking/correction to increase the likelihood of valid data exchange. Each packet includes globally unique source and destination device identifiers to further insure data integrity. Each 'event' packet is tagged with a time stamp for unambiguous correlation of the data 'event' with the physical event producing it.

The local data services infrastructure 22 and the global data services infrastructure 24 all achieve the data integrity goal by holding all measurements until they have been successfully and verifiably transmitted to the next stage in the system.

The system of the present invention is formed of three main subsystems as shown in FIG. 5.
1. Mobile sensors 10 (SIMs, sensor modules).
2. Local Data Services 22 (LDS) infrastructure:
   Data collection wireless access point (AP).
   Local data storage.
   Local data services (analysis, formatting and presentation).
   Local administrator and account services.
3. Global Data Services 24 (GDS) infrastructure:
   Cloud-based server facilities, essential for reliability and scalability.
   Data storage and perpetual archival and back-up.
   Data analysis, formatting and presentation.
   User-account services and revenue management.

In addition, subscribers 26 (local and global) represent the final consumers of all available analytics.

Figure 6:
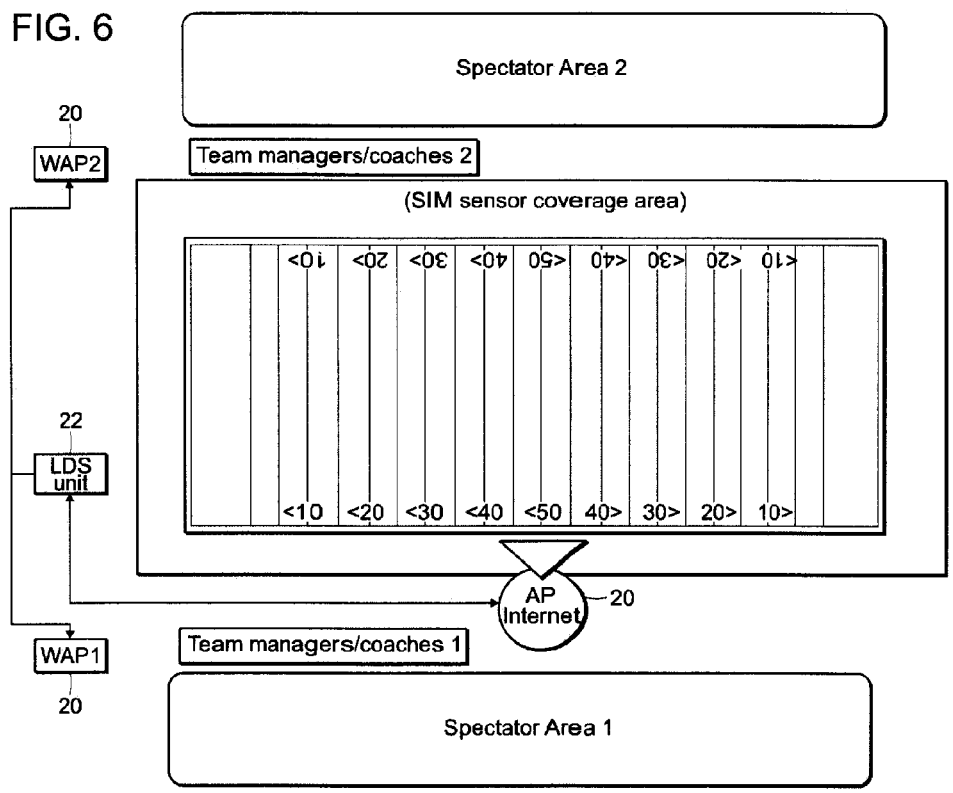
FIG. 6 is a diagrammatic representation of the system of the present invention utilized with an athletic field.

The diagram in FIG. 6 shows a typical football field, with the system installed at the sidelines. In this example, there can be one (shown) or more WAP (WiFi Access Points) 20 to provide adequate WiFi coverage to both sides of the playing field (staff and spectators). Staff for both teams have their own display devices (iPAD, etc.), and are granted access to their respective team's information only.

Figure 7:
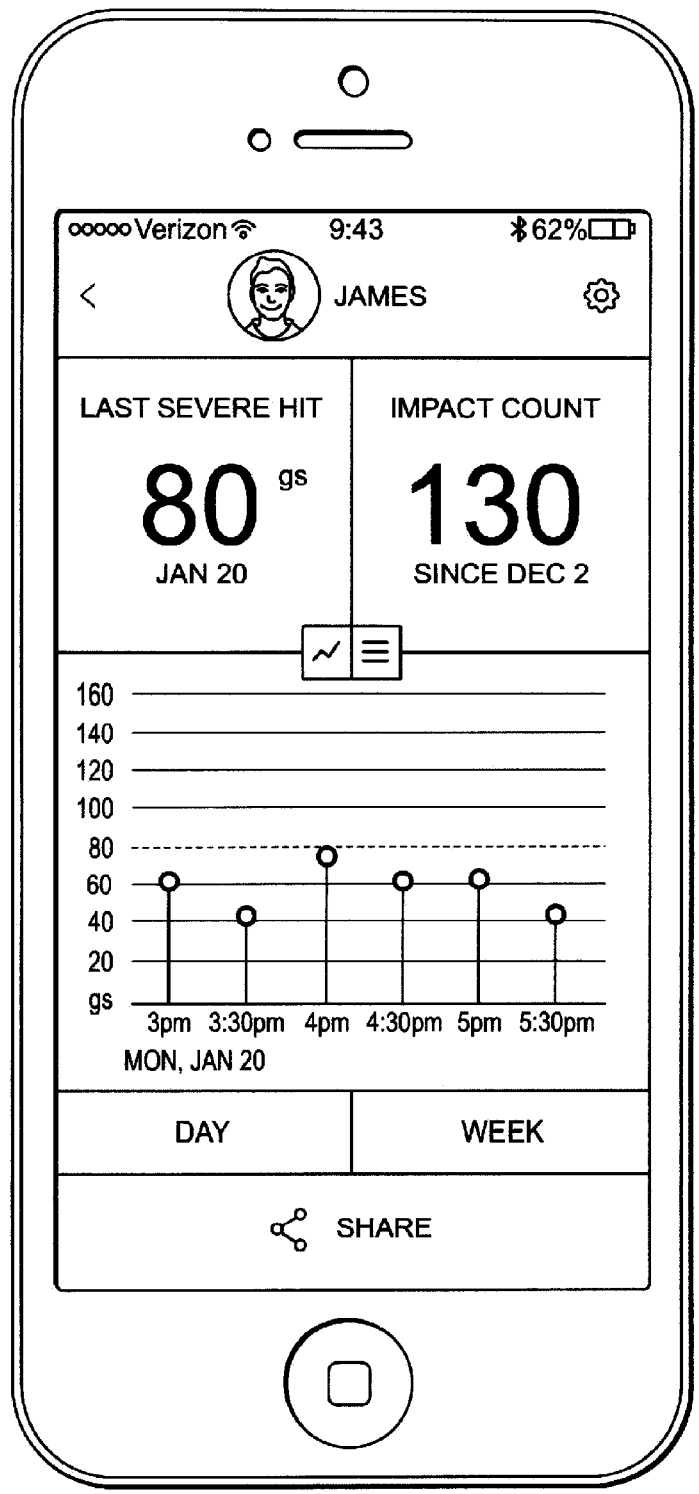
FIG. 7 is a plan view of a display of a PDA, such as a smartphone, displaying data obtained with the system of the present invention for an individual.

The sensor modules each collect data on impact events to the wearer's head that occur during typical sports activities (football, soccer, etc.). The sensor data being recorded includes 3-axis linear accelerometer data, 3-axis rotational data, diagnostics and status, time stamp, and individual device identification as shown in FIG. 7. The sensor modules (SIMs) also contain a small processor that handles sensor data acquisition and manages a wireless radio link with the AP. The SIMs can incorporate a wider and more extensive range of sensor inputs, including standard health monitoring functions (heart rate, respiration, temperature, GSR, etc.) and other physiological parameters.

All impact-event data from the sensor modules are transmitted to the nearby access point via a low-power 900 MHz radio link. The data is received by the AP, processed and presented almost instantaneously to nearby coaches/administrators through the LDS. The LDS infrastructure includes the AP, plus a local computer (PC). This subsystem primarily serves as a real-time data collection and storage unit.

The LDS can be physically deployed at the sidelines, as a mobile LDS or as a fixed LDS at a given sports complex or playing field/stadium/court. In either case, the functionality of the LDS remains the same:
  The AP function block provides the RF link to communicate with all SIM devices within the sports arena.
  The AP streams all SIM data to the LDS unit controller (PC).
  The LDS controller provides bulk local storage for SIM data.
  The LDS controller also provides a limited range of analytics, formatting and presentation services.
    Without an internet connection (access to the GDS), analytics would be limited to the data currently stored in the LDS.
    Local user-access would be via a local WAP device (WiFi Access Point). The analytics are accessed and presented using a common web-GUI interface, using a typical web-browser on a laptop or tablet (or iPhone, iPad, etc.).
    Optionally, the user access can be a custom iPhone/Pad application, rather than using a browser interface. A custom iOS/Android application can be used.
    The LDS services are generally meant for use by the nearby coaches and administrative staff.
The LDS should be connected to the global internet (and thus, the GDS) whenever possible. However, the reality is that many sports venues (football fields, soccer fields, etc.) have little or no access to the global internet, and often lack even AC power.

As an option to a direct internet connection, the LDS can utilize commonly available "LAN/CELL" bridge devices, which allow the use of public cellular networks (GSM, 3G, 4G-LTE, etc.) as the gateway to the internet (and therefore, the GDS). The LAN/CELL bridge devices are generally compatible with a wide range of cellular networks. In most cases, all that is required is a prepaid cellular card plugged into the LAN/CELL bridge unit.

The physical implementation of the LDS has as basic elements, options for fixed or mobile deployments, AC or solar power, battery power, LAN hub, WAP (WiFi-AP), and a cellular-LAN bridge device.
  Some of the features of the present invention include
  For the Mobile LDS:
  Rugged, weather-proof enclosure, suitable for portable hand-carried usage
  Carrying handles.
  Locking cover(s).
  PC based, with integral high-reliability storage units (preferably SSD), able to withstand the rigors of mobile use at sporting events.
  Internal battery supply, sized to provide at least 8 hours of run-time.
  Battery AC charging port: Accepts AC line-voltage input.
  Battery DEPENDENT CLAIM charging port: Accepts typical automotive 12 VDC (nominal) input.
  Video output port: VGA/HDMI/DVI, for attaching a direct console display.
  Antennae port.
  For the fixed LDS:
  Rugged, weather-tight enclosure, suitable for outside use.
  Mounting flanges and fixing hardware suitable for mounting to walls, poles, ceilings.
  Locking cover(s) with security or tamper-evident features and enclosure-access alarm switch.
  PC based, with integral high-reliability storage units (possibly SSD).
  Able to withstand considerable temperature extremes.
  Internal battery supply, sized to provide at least 2 hours of run-time.
  AC input port, for normal operating power.
  An on-board charger to keep the internal battery charged in case it's
  needed.
  Video output port: VGA/HDMI/DVI, for attaching a direct console display.
  Antenna port.
  For networking options:
  LAN port so the LDS can connect directly to a 10/100/1G LAN network.
  WiFi-node so the LDS can connect to a camput-wide wireless network as a client.
  WAP (WiFi AP) so the LDS can provide a local WiFi "network cloud" and the LDS-generated analytics can be accessed locally by coaches on their own laptops or other devices.

The Global Data Services (GDS) subsystem can be considered "cloud based" insofar as it exists as a collection of stored sensor data, programs, and the physical computing hardware could be provided by any number of service providers in this field.

There are many advantages of implementing a "cloud based" design rather than using fixed in-house server hardware implemented using commodity PCs. The key elements of a cloud based strategy can be summarized as follows:
  Location: Server hardware and related data storage facilities can be placed nearly anywhere in the world, wherever operating costs and network accessibility are optimal for the application.
  Reliability: Cloud servers offer much higher operational reliability, and often feature auto-failover to on-site (or remote) backup servers. Failover events are usually transparent to the hosted applications and any attached users.
  Data backups: Automatic backups of data and programs. Proper procedures and facilities management ensures data integrity and security, for both on- and off-site backup archives.
  Scalability: As the underlying dataset grows, and the number of attached users increases, the server architecture will need to scale u accordingly and do so in a manner that does not require a major redesign of either the dataset or the related application programs.
    At the low end, just a fraction of one server (PC) may be utilized by employing a virtual OS "slice" of the available computing power of that one PC.

As requirements grow, dedicated servers and even multiple servers can be utilized to share the attached-user load and access to huge perpetual datasets.

Network access: A large cloud based server will have dedicated top-tier access to the global internet. This will be necessary to efficiently handle the expected number of subscribers.

Infrastructure: The facilities, power, cooling and security are all managed and cost-optimized not just for one or a few servers, but for an entire server-farm encompassing potentially many thousands of servers.

Site Backup: High availability cloud service providers often provide geographically diverse locations. This enables a rapid cutover and recovery from catastrophic events (earthquakes, floods, etc.).

The SIM sensors, AP+LDS, and GDS, together form a system whose primary purpose is data collection, storage, analysis and presentation.

A key element of the system is the acquisition and perpetual long-term storage of all available sensor (SIM) data. Over time, no doubt there will be many ways of analyzing that data for various purposes. Sometimes for the user's own personal "performance monitoring" needs. At other times, the data will be invaluable for analysis of athletic performance and related injuries, correlating with demographics other recorded factors.

Figure 8:
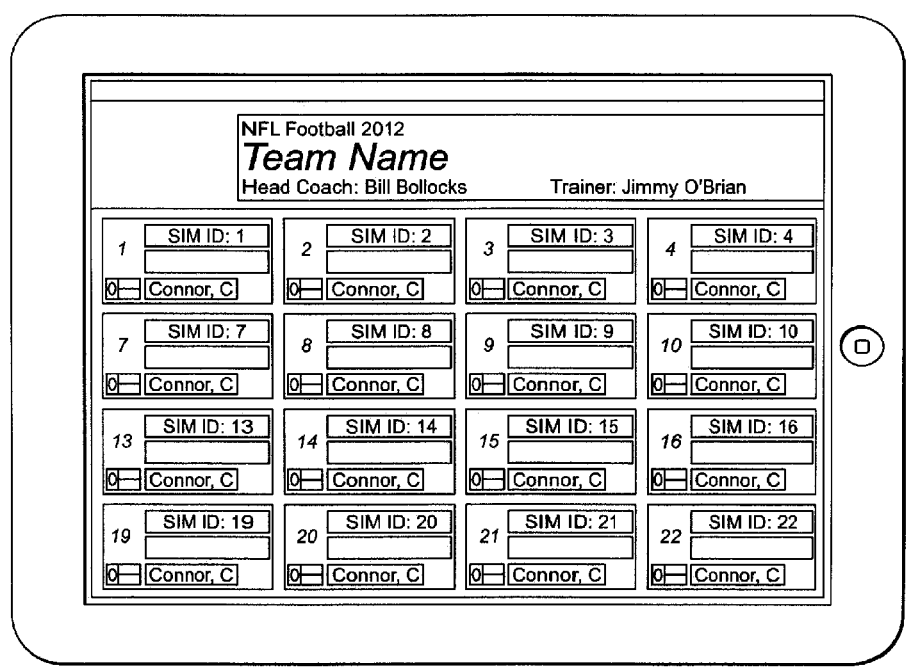
FIG. 8 is a plan view of a computer display of data obtained with the system of the present invention for a plurality of individuals.

FIG. 8 shows a user interface which can be used as an exemplary layout of a sensor-event record, as it would be stored (locally) in the LDS, and transferred to/from the GDS (and stored there as well). The sensor-event record, as shown, contains discrete fields which are, in most cases, simply extracted from the raw sensor-event data (as delivered over the RF link). These discrete fields are brought out so that the LDS/GDS database engine (mySQL, etc.) can use those fields to efficiently index and organize the records. Whether the data storage (on disk) is a "relatively small" database like on the LDS, or scaled up to "multi-terabyte" database (on the GDS), it is important to bring out some fields like this because the database engine is most efficient at what it does best—indexing and accessing data organized into fields. On the LDS there will be a single SQL (or other) program managing event records. On the GDS, the equivalent "SQL engine" function can easily be scaled up to many servers, all accessing the same storage unit, providing analytics for many thousands of users worldwide. Keeping the event-record the same everywhere keeps things uniform. The system relies not only on the sensor data, but a number of interrelated databases which ensure the proper identification, storage, categorization, analysis and distribution of the results. The sensor event records are stored and managed by the database engine (SQL, etc.), using one or more of the "-ID" fields as primary index keys. The user database contains detailed user identification (name, address), and a list of all SIM-ID/IDX's that have been assigned to this user.

Each organization (school, university, club, etc.) will be registered into the system, and each organization will be responsible for one or more AP+LDS units. Each AP+LDS unit will be registered and activated before it can participate in the system. This is mainly to prevent the use of unauthorized copies of the LDS.

The subscriber database authenticates the final consumers of the sensor data and its derivative analytics. Subscribers are pay-for-access users, and therefore a related mechanism will be the billing and user-account management for each subscriber. There will be various subscriber access levels.

The most common access method, generally compatible with most if not all devices, is a typical browser-based GUI. It would be accessed by a fixed URL. The browser interface GUI should be straightforward and as simple as possible in terms of using the "special features" of any particular browser. In fact, all analytics should be delivered as graphic images (JPEG/GIF/PNG) that are computed and delivered as needed. Some of the browsers to support include:

IE (Microsoft, version 6+)
Safari (Apple)
Opera (PC and mobile)
Google Chrome
Firefox The browser GUI interface should be similar to the "large tablet" version of the iOS/Android apps, taking full advantage of a much larger screen. Also, browser access usually means that printing of analytics will be possible.

The following is a general description of data flow activities within the LDS

1. The LDS Windows-app:
   a. Receive sensor data from the AP (RF-link).
   b. Unscramble or otherwise decrypt, then validate, the data.
   c. Create standardized "sensor event records".
   d. Store these records on the local hard-drive using the resident database engine (mySQL, etc,).
   e. Act as an admin-console for configurations settings in the system.
   f. Generates requested analytics from the local database.
   g. Cache all requested analytics. These will be used locally by the web-server and app-server delivery subsystems.
   h. Upload any new sensor-event records to the GDS.
      i. Local sensor-event caching should have an admin-configurable "cache size" setting. Usually it will be set to "limited to disk space", but in some cases it might be "limited to the last 12 months of data".
   i. Download sensor-event records from the GDS, for any analytics-requests which require sensor-event records which aren't already stored locally.
   j. Manage user-registration (assignment of SIMs).
   k. Manage user and subscriber authentication.
      i. Download account data and credentials from the GDS whenever possible.
      ii. It will be necessary to locally cache user/subscriber credentials, since the LDS will likely not have a permanent internet connection to the GDS.

One or more of the following software capabilities can be used:

2. A resident web-server will serve analytics to locally connected (via LAN or localized WiFi cloud) subscribers that are accessing the system using a web-browser.
3. A resident iOS app-server will serve analytics to locally connected (via LAN or localized WiFi cloud) subscribers that are accessing the system using an iOS device.
4. A resident Android app-server will serve analytics to locally connected (via LAN or localized WiFi cloud) subscribers that are accessing the system using an Android device.
5. A resident Windows Phone app-server will serve analytics to locally connected (via LAN or localized WiFi cloud) subscribers that are accessing the system using a Windows Phone device.

The following is a general description of programs running on the GDS (via a Cloud Service):

1. Operating system.
2. A database engine.
3. LDS host-side server module.

4. Web server module.
    a. Any web server-related plug-ins and support programs (PHP, Perl, Java, Python, etc.) that may be necessary.
    b. The custom "website" (HTML and support files), designed to implement a web-based GUI. This would be designed to look very similar (but not identical) to the LDS version.
5. iOS Application Server module.
6. Android Application Server module.
7. Windows Phone application server module.

The following is a general description of activities within the GDS:

1. LDS host-side server.
    a. Manage connections to remote LDS units.
    b. Upload/download sensor even records, as requested by the remote LDS s.
    c. Store/retrieve these records using the resident database engine (mySQL, etc.).
    d. Generates requested analytics from the local database.
    e. Cache all requested analytics. These will be used by the web-server and app-server delivery subsystems.
    f. Manage user and subscriber authentication as requested by the remote LDS s.
    g. Interface with the subscriber billing and account management system.
2. The resident web-server will serve analytics to internet-connected subscribers that are accessing the system using a web-browser.
3. The resident iOS app-server will serve analytics to internet-connected subscribers that are accessing the system using an iOS device.
4. The resident Android app-server will serve analytics to internet-connected subscribers that are accessing the system using an Android device.
5. The resident Windows Phone app-server will serve analytics to internet-connected subscribers that are accessing the system using a Windows Phone device.

There are many possible ways of analyzing sensor-data, from real-time events (at a football game), to more generalized statistical research.

Figure 9:
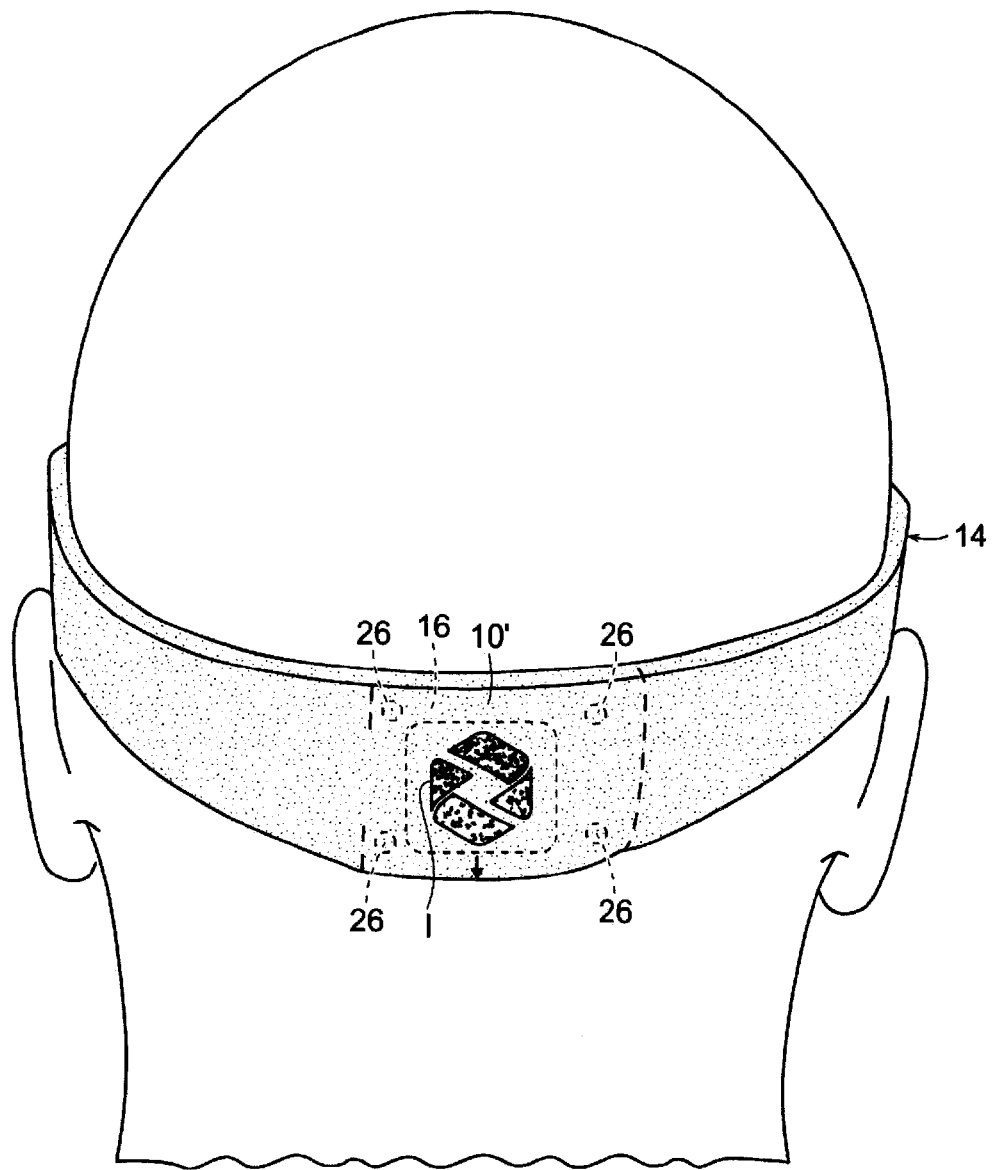
FIG. 9 is a rear view of a headband carrying a sensor module according to the present invention positioned on the rear of the skull of an individual.

A variation of the present invention is illustrated in FIG. 9 wherein the sensor module 10' has an antenna within the housing thereof such that an arcuate space for the antenna in the headband is not required. Additionally, arrow indicia is displayed on the outer surface of the headband at the pocket receiving the sensor module 10' to assure that the individual wearing the headband has vertically properly aligned the headband and the accompanying sensor module. Additionally, portions of non-Newtonian fluid are positioned on the inner surface of the headband to separate the skull from the sensor module. The non-Newtonian fluid, in one example, will be supplied in four small ovals sewn into the inner lining of the headband SIM pocket. The non-Newtonian fluid will be a small buffer against the SIM and the back of the head which will allow the SIM to generate a more accurate impact reading.

From the above, it should be appreciated that the present invention permits continuous sampling and recording of high-g accelerometer and gyro data since, when an impact/event is detected, the data that was recorded at the impact point is transmitted along with data relating to what happened before the impact. More particularly, high-g accelerometer (linear) and gyroscope (rotation) are sampled/monitored at, for example, a 1 KHz rate and successive samples of the linear and rotational sensor data are placed in a circular buffer. The system of the present invention can be used in conjunction with specialized software to perform a cognitive and balance evaluation test when data indicates that such tests are desirable.

The above described embodiments of the present invention can be varied as will be understood by one of ordinary skill in the art, for example, use of different radio frequencies and radio transmission chips and circuits for data transmission, inclusion of additional sensors and sensing capabilities within the sensor module, use of alternative power sources permitting charging mechanisms such as induction charging, and motion-based energy "harvesting". Additionally, the present invention can utilize cell phones, tablet computers, laptop computers or other similar devices as an alternative to a dedicated LDS system for example using Bluetooth or WiFi for communication with the sensor modules, the use of a self-contained LDS system including integral computing capability but not including an external laptop computer device, a system using a "self-contained" LDS incorporating some elements of functionality from the GDS to allow use without a GDS system. Alternative designs could also utilize a general purpose network technology (rather than one specifically deployed for the application of the present invention within an LDS) examples of which would be a WiFi network, cellular phone or paging network and a general purpose data communications network such that alternative designs could include a system without and LDS but where some of the functionality of the LDS is moved to the GDS. Allow correlation with the axes in the sensor module.

Inasmuch as the present invention is subject to many variations, modifications and changes in detail, it is intended that all subject matter discussed above or shown in the accompanying drawings be interpreted as illustrative only and not be taken in a limiting sense.

The invention claimed is:

1. An assembly for sensing forces to a head of an individual comprising
    a flexible support having a shape to surround at least a portion of the head of the individual; a sensor module attachable to the flexible support, the sensor module configured to sense forces experienced by the head of the individual in three orthogonal axes, and communicate one or more signals of the forces sensed in the three orthogonal axes;
    a wireless transmitter incorporated in the sensor module for transmitting the one or more signals;
    the sensor module further comprising at least one processor configured to analyze force signals sensed by the sensor module and trigger communication of a first signal and a second signal of the one or more signals of the forces responsive to detecting forces exceeding a predetermined threshold to a remote device, wherein the first signal is representative of forces sensed during a first time period prior to detecting forces exceeding the predetermined threshold and the second signal is representative of forces sensed during a second time period after detecting forces exceeding the predetermined threshold.

2. The assembly of claim 1, wherein the flexible support is formed by an elastic headband.

3. The assembly of claim 2, wherein said headband includes a membrane for covering the top of the head to form a skullcap.

4. The assembly of claim 2, wherein the headband further comprises a non-stretchable material.

5. The assembly of claim 2, wherein the headband further comprises an inner surface and at least one non-Newtonian fluid portion positioned on the inner surface to buffer the sensor module and a back of the head.

6. The assembly of claim 5, wherein the at least one non-Newtonian fluid portion is configured to thicken responsive to impact on the individual and facilitate accurate sensing of forces to the head.

7. The assembly of claim 1, wherein the flexible support includes an elastic.

8. The assembly of claim 1, wherein the flexible support is constructed and arranged to limit double hit sensing in response to an impact on the individual.

9. The assembly of claim 1, wherein the flexible support further comprises at least one non-stretchable portion and at least one stretchable portion, wherein the at least one stretchable portion is smaller in at least one dimension than the at least one non-stretchable portion, and the at least one stretchable portion is configured to conform to the head.

10. The assembly of claim 1, wherein the wireless transmitter is configured to transmit the one or more signals determined to be over the predetermined threshold in real time for the forces sensed.

11. The assembly of claim 10, further comprising a local data service infrastructure located at a physical location near the sensor module, wherein the sensor module is configured to transmit signals in real-time to the local data service infrastructure permitting the formatting and presentation of the transmitted data.

12. The assembly of claim 11, further comprising a global data service infrastructure located at one or more physical locations remote from the sensor module, wherein the local data service infrastructure is configured to transmit signals to the global data service infrastructure.

13. The assembly of claim 11, wherein the local data service infrastructure comprises an authentication service to permit selective access to the sensor data and derivative analytics of the sensor data.

14. The assembly of claim 1, wherein the sensor module carried by the support at a location for sensing forces experienced by the head of the individual in three rotational axes and three linear axes.

15. The assembly of claim 1, wherein the flexible support having the shape to surround at least the portion of the head of the individual is attached to a helmet worn by the individual.

16. A method for monitoring impact forces applied to a head of an individual, the method including the steps of:
    detecting, by a sensor module positioned at a posterior position of the head of the individual, impact forces experienced by the head of the individual;
    analyzing, by at least one processor in the sensor module, detected impact forces to identify any of the impact forces above a predetermined threshold; and
    transmitting, by a wireless transmitter, a first signal and a second signal of the detected impact forces to a remote device, wherein the first signal is representative of impact forces detected during a first time period prior to an identified impact force exceeding the predetermined threshold and the second signal is representative of impact forces detected during a second time period after the identified impact force exceeding the predetermined threshold.

17. The method of claim 16, wherein the method further comprising limiting by a flexible support double hit sensing in response to an impact on the individual.

18. The method of claim 16, further comprising securing the sensor module to the head of the individual with a the flexible support comprising at least one non-stretchable portion and at least one stretchable portion, wherein the at least one stretchable portion is smaller in at least one dimension than the at least one non-stretchable portion, and the at least one stretchable portion is configured to conform to the head.

19. The method of claim 16, wherein transmitting by the wireless transmitter is executed for the first signal and the second signal in real time for the detected impact forces.

20. The method of claim 19, further comprising transmitting to an associated local data service infrastructure at a physical location near the sensor module.

21. The method of claim 16, further comprising generating in a user interface a histogram display of transmitted forces over time, wherein generating in the user interface includes generating a visual indicator of a last severe hit.

* * * * *